(12) United States Patent
Baetz et al.

(10) Patent No.: US 6,341,156 B1
(45) Date of Patent: Jan. 22, 2002

(54) X-RAY DIAGNOSTIC APPARATUS WITH RELATIVELY MOVED X-RAY SOURCE AND DETECTOR

(75) Inventors: Lothar Baetz, Heroldsberg; Wolfgang Haerer, Litzendorf; Thomas Mertelmeier, Erlangen, all of (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/568,545

(22) Filed: May 11, 2000

(30) Foreign Application Priority Data

May 14, 1999 (DE) .......................................... 199 22 346

(51) Int. Cl.⁷ .............................. A61B 6/03; H05G 1/64
(52) U.S. Cl. ............................ 378/98.8; 378/4; 378/196
(58) Field of Search ................................ 378/98.8, 193, 378/195, 196, 197; 350/4, 11, 370.09

(56) References Cited

U.S. PATENT DOCUMENTS

| | | |
|---|---|---|
| 4,149,082 A | 4/1979 | Haendle et al. |
| 5,510,622 A | 4/1996 | Hu et al. ..................... 250/367 |
| 5,523,554 A | 6/1996 | Hassler et al. ......... 250/370.09 |
| 5,737,382 A | 4/1998 | Stierstorfer ..................... 378/4 |
| 6,215,848 B1 * | 4/2001 | Linders et al. ............. 378/98.8 |
| 6,363,043 * | 7/2001 | Maschke ..................... 378/209 |

FOREIGN PATENT DOCUMENTS

DE   OS 196 13 663   10/1997

\* cited by examiner

Primary Examiner—Drew Dunn
(74) Attorney, Agent, or Firm—Schiff Hardin & Waite

(57) ABSTRACT

In an x-ray diagnostic apparatus for tomosynthesis or laminographic imaging using a patient positioning table, an x-ray source which emits an x-ray beam on one side of the patient positioning table, an x-ray detector arranged on the other side of the patient positioning table for the capture of the x-ray beam and for producing digital images, a device for movement of the x-ray source, a device for shifting of the x-ray detector and a device for superimposing the digital images so that only the details lying in a specific longitudinal slice for an examination subject are sharply imaged, the x-ray detector is rotated relative to the movement direction at an angle.

10 Claims, 3 Drawing Sheets

X-RAY DIAGNOSTIC APPARATUS WITH RELATIVELY MOVED X-RAY SOURCE AND DETECTOR

BACKGROUND OF THE INVENTION

1. Field of the Invention

The present invention is directed to an x-ray diagnostic apparatus for tomosynthesis or laminographic imaging with a patient positioning table, with an x-ray source which emits an x-ray beam on one side of the patient positioning table, an x-ray detector arranged on the other side of the patient positioning table for capturing the x-ray beam and for producing digital images, a device for moving the x-ray source, a device for adjusting the x-ray detector, and a device for superimposing the digital images so that only the details of an examination subject disposed in a specific longitudinal slice are sharply imaged.

2. Description of the Prior Art

An x-ray diagnostic apparatus of this type is known, for example, from German OS 27 12 320, corresponding to U.S. Pat. No. 4,149,082 wherein images of a specific slice of a patient lying on a patient positioning table are produced as a result of the movement of the x-ray beam. Only those points are thereby sharply imaged that lie in the selected slice plane. Points in the body of the patient that lie above or below the selected slice plane are automatically precluded from contributing to the image, due to the movement of the x-ray beam, so that they are not perceptible.

A digital solid-state flat detector with radiation-sensitive elements formed by amorphous silicon arranged in a matrix configuration is disclosed, with an indirect x-ray converter, such as, for example, a scintillator composed of caesium iodide (CsI) has recently been developed for radiography and fluoroscopy. Digital solid-state flat detectors having a direct x-ray converter, such as e.g. selenium, are also known. Such flat detectors generate an image signal in digital form, corresponding to the resolution produced by the number of elements. For this reason, they are well-suited for the digital further processing of the image signals and in particular, also for the use of reconstructive methods. Tomosynthesis, laminographic imaging, or classical tomography each represent such a reconstructive imaging method, that is also called digital tomosynthesis given digital processing.

Due to the production process and the complex read-out electronics, these new digital detectors customarily exhibit faults that can be amplified in the processing of the signals. Such faults can cause individual, dropped out pixels or pixel groups as well as vertical and horizontal stripe patterns, referred to as offset faults and readout electronic stripes.

These artifacts are particularly disruptive given tomosynthesis, wherein the individual projections are conventionally acquired with very low dosage and the radiography detector used, among others, is specified for higher dosage values with respect to the faults. In digital tomosynthesis, individual exposures of a subject are made from different viewing directions that are subsequently shifted and summed. To improve image quality, the exposures are often digitally filtered before or after the superimposition using filters that usually exhibit a high pass characteristic and operate in the scanning direction. Since n individual projections are added for the preparation of the overall image, the x-ray dosage of an individual projection approximates an $n^{th}$ of that of the overall image. Customarily, n lies in the range between 10 and 100 so that a very low dosage value results for an individual projection. Given such limited dosage values, however, the described faults become particularly conspicuous. The fault specifications for the detectors are mostly oriented to the customary, radiographic exposure requirements, i.e. at essentially higher dosage values than are required for the tomosynthetic individual projections.

Given the flat detectors used heretofore for projection radiography, either a preprocessing is implemented using appropriate calibration and correction software, or the faults are limited such that they can be tolerated given the radiographic and fluoroscopic dosage values used. The requirements for the quality of the detectors with respect to the artifacts is then higher, the lower the prescribed dosage is. No routine application using grossly planar, solid-state flat detectors is known for such low dosage values as are required for the tomosynthetic individual projections.

An x-ray detector arrangement for CT-scanning systems is known from German OS 195 25 605, wherein the individual detector elements have a parallelogram-type input surface. The goal of this type of structure is to reduce the effective distance of the individual detector elements, whereby the topical resolution can be increased. The detector elements are arranged in a parallelogram grid that has, as a result, a specific structurally determined grid arrangement of the elements.

SUMMARY OF THE INVENTION

An object of the present invention is to provide an x-ray diagnostic apparatus of the type described above that, without pre-processing, is insensitive to artifacts arising from detector errors.

The object is inventively achieved in an apparatus wherein the x-ray detector is rotated relative to the tomosynthesis direction or the slice direction by an angle $\alpha$. As a result of the rotation of the flat detector at an angle a within the detector plane relative to the tomosynthesis direction or slice direction of the x-axis, vertical and horizontal stripe shaped detector faults are not noticeable, for example, or are at least strongly suppressed since they are approximately averaged out. A two-dimensional detector of conventional structure having a rectangular intrinsic scanning grid is rotated at an angle against the scanning direction.

It has proven to be advantageous for the x-ray detector to be a digital large area solid-state flat detector.

In accordance with the invention, the angle a can lie in the range of 2° to 88°, particularly 5° to 20°, preferably 10°.

It is advantageous for the angle a of the flat detector to be adjustable depending on the operating mode, artifact structure, readout means of the specifically observed detector and tomosynthesis movement so that it can be optimally adapted to each situation. The angle $\alpha$ of the flat detector is variably adjustable from individual projection to individual projection. As a result, it becomes possible to use the detector non-rotated in the radiography operation. In the tomosynthesis mode, the angle a can be optimized according to the artifact structure, readout direction of the specifically observed detector and tomosynthesis movement. Also, an angle that is variable from individual projection to individual projection can be attained.

Besides a normal x-ray diagnostic apparatus, a C-arm device can also be used according to the invention.

It has proven to be advantageous for the x-ray source to be moved in a first direction and the x-ray detector is oppositely moved in a second direction opposite that of the first. Alternatively, the x-ray source and the x-ray detector move isodirectionally in the same direction.

DESCRIPTION OF THE PREFERRED EMBODIMENTS

Figure 1:
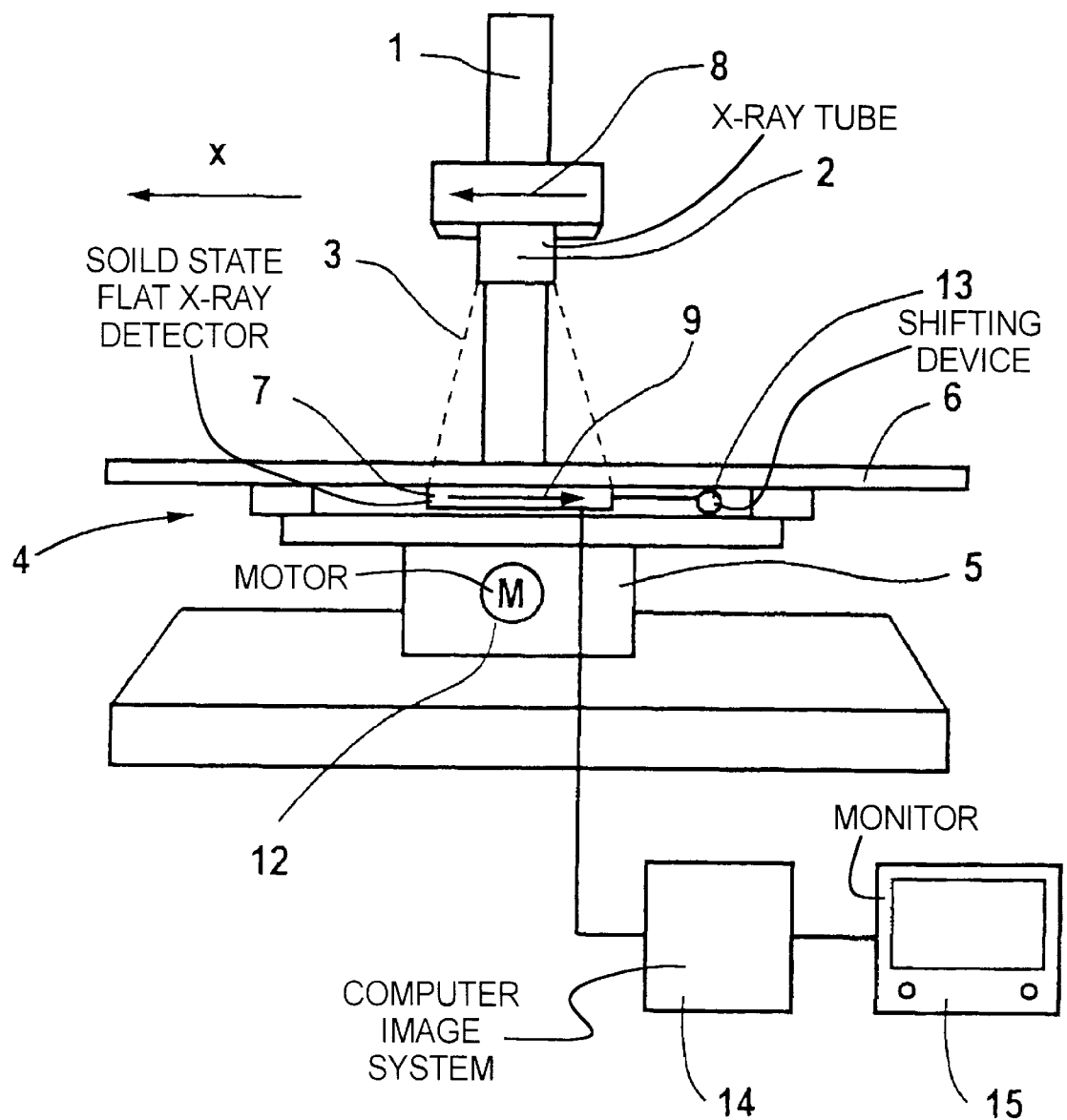
FIG. 1 is a schematic illustration of an x-ray device for tomosynthesis, in which the present invention can be used.

In FIG. 1, an x-ray diagnostic apparatus is shown that has an x-ray tube 2 attached at a support 1 that emits an x-ray beam 3 directed downwardly. An adjustable patient positioning table 4 is attached at a base 5. A digital solid-state flat detector 7 is adjustably arranged under the positioning plate 6 of the patient positioning table 4.

For the preparation of tomosynthesis exposures or tomograms, the x-ray source and the detector are moved in opposite directions or in the same direction, as is shown by the arrow 8 for the x-ray tube 2 and by the arrow 9 for the flat detector 7 for the frequent case of an oppositional movement. The movement of the x-ray tube 2 can ensue by rotating the support 1 by means of a motor 12, or the support 1 can be shifted and the x-ray tube 2 rotated. The flat detector 7 is linearly shifted below the positioning plate 6 by means of a device 13. The x-ray tube 2 is moved such that its x-ray beam is always incident on the flat detector 7. A digital image computer system 14 is connected to the flat detector 7, the output of which is supplied to a monitor 15 as a playback device for the x-ray images. The x-ray device can alternatively have a C-arm that can be rotated.

Figure 2:
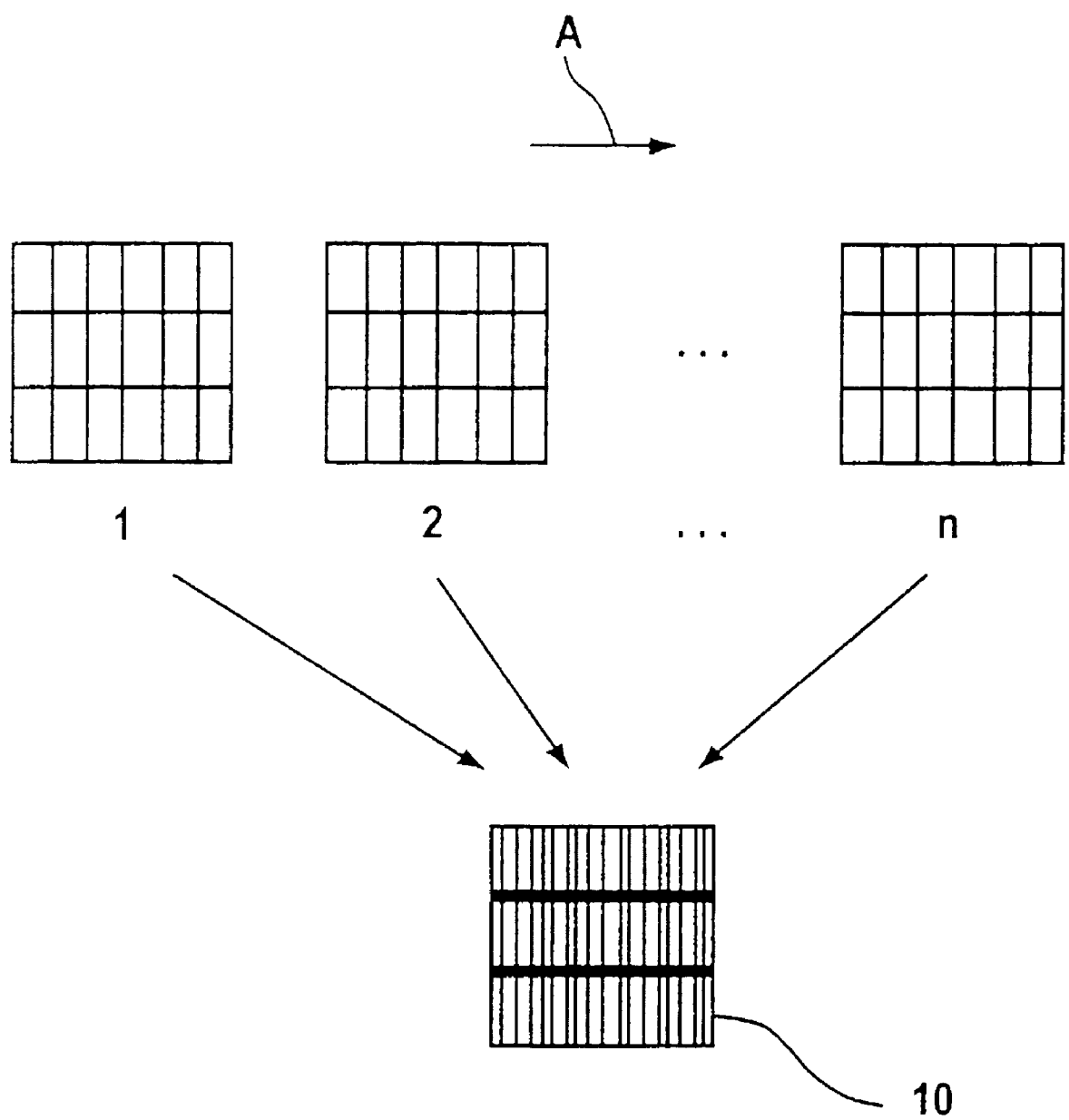
FIG. 2 is a schematic representation of the superimposition of the images in accordance with the prior art.

The disadvantages of an x-ray diagnostic means according to the prior art given a non-rotated detector are explained on the basis of FIG. 2. For the preparation of tomosynthesis exposures or tomograms, 1, 2 ... n, individual projections are prepared in the scanning direction A from different angles and are stored in the image system 14. These exposures are horizontally shifted for the processing in the computer image system 14 so that the desired image points of a slice are brought into registration and are added. For improvement of the image quality, filtering frequently is undertaken before or after this superimposition, generally with a high pass filter in the scanning direction. Given linear tomosynthesis movement in a horizontal direction, the horizontal stripe faults are not suppressed since they accumulate (add). The image content of the individual projections as well as the tomosynthesis exposure is not shown, merely the stripe faults are displayed. In the case of filtering with a high pass characteristic in the direction of the tomosynthesis movement, the vertical stripes are first amplified by the edge enhancing effect of the filter.

Without rotating the detector, these vertical stripes appear due to the shifting of the digital individual image by a value determined by the tomosynthesis angle in the resulting aggregate image at different positions and as a result they are barely noticeable in totality due to the accumulation of many individual images, even when applying the above-described filtering. In contrast, horizontal stripes in the individual projections are independently amplified by filtering (if used) due to the detector shifting in the same horizontal direction. As a result, the image impression of a horizontal artifact stripe extended into the x-direction results after reconstruction.

Figure 3:
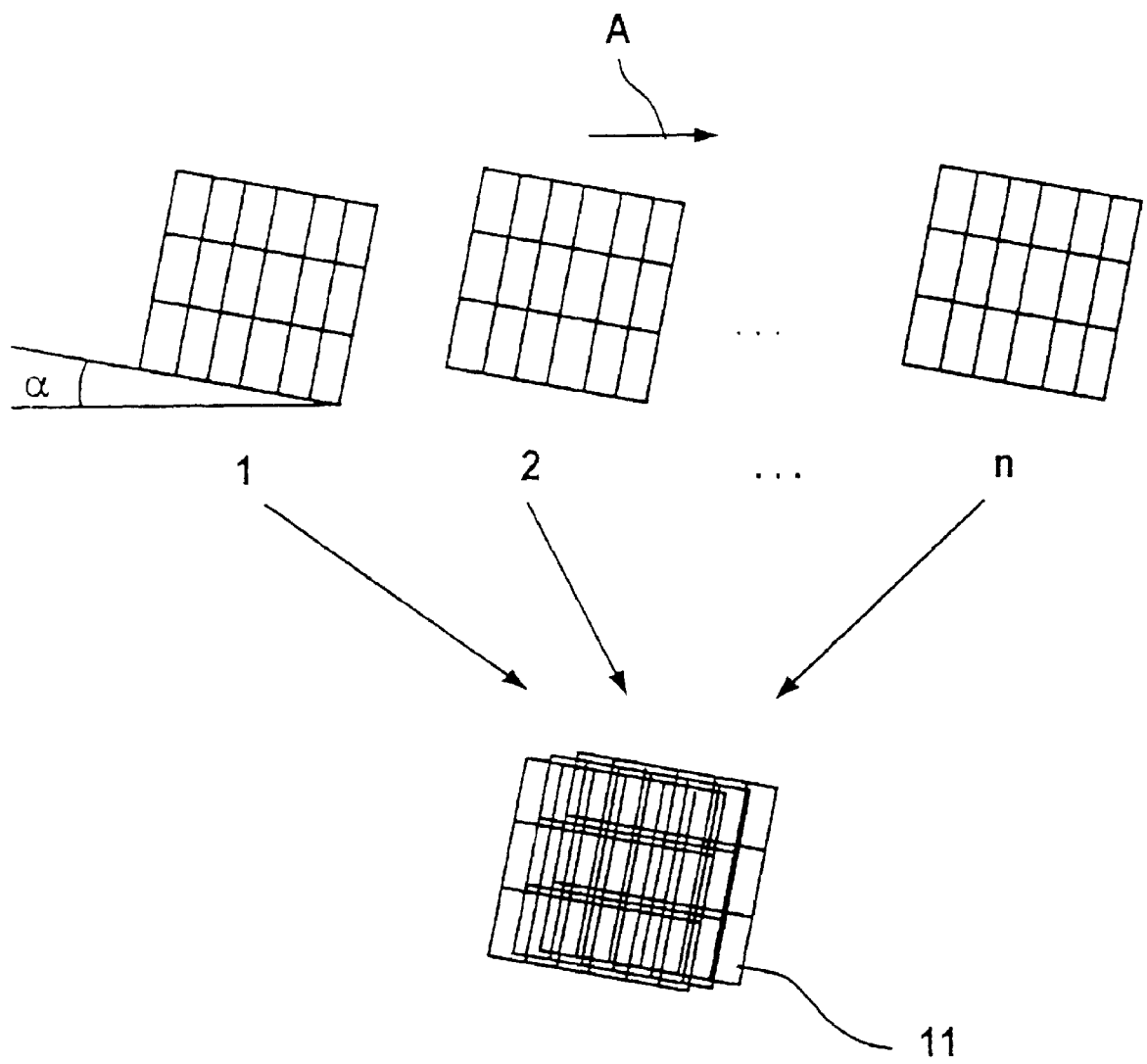
FIG. 3 is a schematic representation of the inventive superimposition of the images.

To avoid such problems, the solid-state flat detector 7 is inventively turned at an angle α of, e.g. 10° relative to the tomosynthesis direction or slice direction x. Given this rotated detector, shown in FIG. 3, the horizontal stripe faults given the same exposure and processing requirements are suppressed given linear tomosynthesis movement in a horizontal direction, since they appear at different places in the overall image and thus cannot be seen due to the slight contribution of 1/n to the overall image.

This flat detector is installed in the housing or detector holder below the positioning plate 6 of the patient positioning table 4, given a horizontal slice direction or tomosynthesis movement in the x-direction rotated at an angle a relative to the x-axis. The vertical stripes continue to be summed at various places and so remain as a result without effect. The horizontal stripes are, however, also summed at various places due to the detector turning and remain, therefore, also without effect. In this case, even high-pass filtering in a horizontal direction, if used, remains approximately without effect on the horizontal stripes, given a just a slight rotation.

If the x-ray diagnostic apparatus is used in the radiography mode, the detector can be used unrotated. In the tomosynthesis mode, the angle a can be optimized according to the artifact structure or readout direction of the detector and tomosynthesis movement being employed. The x-ray diagnostic apparatus also can be fashioned such that the angle a of one individual projection to another can be changed.

By means of the inventive construction of the x-ray diagnostic apparatus, good artifact suppression given linear digital tomosynthesis using a digital flat detector is obtained.

If a C-arm device is used as the x-ray device, an artifact reduction can be attained using this inventive construction even using other reconstructive imaging techniques, such as, e.g. cone-beam-CT using Feldkamp-based reconstruction algorithms.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostic apparatus comprising:

positioning table adapted to receive a subject;

an x-ray source, which emits an x-ray beam, disposed at a first side of said positioning table;

a digital x-ray detector disposed on a second side of said positioning table, opposite said first side, so that said x-ray beam, after penetrating a subject, is incident on said digital x-ray detector, said digital x-ray detector comprising a plurality of imaging elements disposed in a matrix which emit output signals dependent on x-rays incident thereon;

a device for producing relative movement between said x-ray source and said digital x-ray detector along a movement direction;

a computerized imaging system supplied with said output signals from said digital x-ray detector for producing a plurality of digital images therefrom, and for superimposing said digital images to produce a superimposed image wherein details only within a specified longitudinal slice of said subject are sharply imaged; and said x-ray detector being rotated at an angle relative to said movement direction.

2. An x-ray diagnostic apparatus as claimed in claim 1 wherein said digital x-ray detector is a large area solid-state flat detector.

3. An x-ray diagnostic apparatus as claimed in claim 1 wherein said angle is between 2° and 88°.

4. An x-ray diagnostic apparatus as claimed in claim 1 wherein said angle is between 5° and 20°.

5. An x-ray diagnostic apparatus as claimed in claim 1 wherein said angle is 10°.

6. An x-ray diagnostic apparatus as claimed in claim 1 wherein said x-ray source and said digital x-ray detector are operable in a plurality of imaging modes, and wherein said superimposed image is subject to different artifacts, and wherein said computerized imaging system reads out said digital x-ray detector in a readout mode, and wherein said device for producing relative movement between said x-ray source and said digital x-ray detector produces different types of movements, and wherein said angle is adjustable dependent on at least one of said operating mode, said artifact, said readout and said movement.

7. An x-ray diagnostic apparatus as claimed in claim 1 wherein said angle is adjustable from digital image to digital image.

8. An x-ray diagnostic apparatus as claimed in claim 1 further comprising a C-arm on which said x-ray source and said digital x-ray detector are mounted.

9. An x-ray diagnostic apparatus as claimed in claim 1 wherein said device for producing relative movement comprises a first unit for moving said x-ray source in a first direction and a second unit for moving said digital x-ray detector in a second direction, opposite to said first direction.

10. An x-ray diagnostic apparatus as claimed in claim 1 wherein said device for producing relative movement comprises a first unit for moving said x-ray source in a first direction and a unit for moving said x-ray detector also in said first direction.

* * * * *